(12) United States Patent
Dubach

(10) Patent No.: US 9,907,919 B2
(45) Date of Patent: Mar. 6, 2018

(54) LARYNGEAL MASK HEAD

(71) Applicant: Singularity AG, Maur (CH)

(72) Inventor: Werner F. Dubach, Maur (CH)

(73) Assignee: SINGULARITY AG, Maur (CH)

( * ) Notice: Subject to any disclaimer, the term of this patent is extended or adjusted under 35 U.S.C. 154(b) by 557 days.

(21) Appl. No.: 14/405,394

(22) PCT Filed: May 29, 2013

(86) PCT No.: PCT/EP2013/061059
§ 371 (c)(1),
(2) Date: Dec. 3, 2014

(87) PCT Pub. No.: WO2013/182460
PCT Pub. Date: Dec. 12, 2013

(65) Prior Publication Data
US 2015/0114400 A1    Apr. 30, 2015

(30) Foreign Application Priority Data

Jun. 4, 2012 (CH) .......................... 768/12
Jul. 26, 2012 (CH) ....................... 1169/12

(51) Int. Cl.
*A61M 16/00* (2006.01)
*A61M 16/04* (2006.01)
*A61M 16/20* (2006.01)
A61M 16/08 (2006.01)

(52) U.S. Cl.
CPC ........ *A61M 16/0447* (2014.02); *A61M 16/04* (2013.01); *A61M 16/0409* (2014.02); *A61M 16/0497* (2013.01); *A61M 16/20* (2013.01); *A61M 16/0816* (2013.01)

(58) Field of Classification Search
CPC .......... A61M 16/0447; A61M 16/0486; A61M 16/0816; A61M 2207/10; A61M 16/04; A61M 16/0409; A61M 16/0497; A61M 16/20; B29C 45/36
See application file for complete search history.

(56) References Cited

U.S. PATENT DOCUMENTS

| 6,070,581 | A | | 6/2000 | Augustine et al. | |
|---|---|---|---|---|---|
| 6,095,144 | A | * | 8/2000 | Pagan .................. | A61M 16/04 128/207.14 |
| 6,439,232 | B1 | * | 8/2002 | Brain ................... | A61M 16/04 128/200.26 |
| 6,546,931 | B2 | * | 4/2003 | Lin .................. | A61M 16/0409 128/204.18 |

(Continued)

FOREIGN PATENT DOCUMENTS

EP    1875937 A2    1/2008

*Primary Examiner* — Steven Douglas
(74) *Attorney, Agent, or Firm* — DWC Law Firm, P.S.; Ann W. Speckman; David Chen

(57) ABSTRACT

Especially during emergencies, there is a need for laryngeal mask heads with a ventral respiration chamber that has a cuff which surrounds the respiration chamber and which can be adjusted in size without having to be inflated. To meet said need, the laryngeal mask head comprises non-pneumatic structures to adjust the size of the mask head in the medial-lateral direction and the ventral-dorsal direction, which are preferably implemented by open, resilient channels extending in the same direction as the cuff.

17 Claims, 6 Drawing Sheets

(56) References Cited

U.S. PATENT DOCUMENTS

| | | | |
|---|---|---|---|
| 2004/0020491 A1* | 2/2004 | Fortuna | A61M 16/04 128/207.15 |
| 2006/0102186 A1 | 5/2006 | Adler | |
| 2008/0099026 A1* | 5/2008 | Chang | A61M 16/0493 128/207.15 |
| 2011/0220117 A1* | 9/2011 | Dubach | A61M 16/04 128/207.14 |
| 2011/0226256 A1* | 9/2011 | Dubach | A61M 16/04 128/207.14 |
| 2012/0090609 A1* | 4/2012 | Dubach | A61M 16/04 128/204.18 |
| 2015/0114400 A1* | 4/2015 | Dubach | A61M 16/04 128/207.15 |

\* cited by examiner

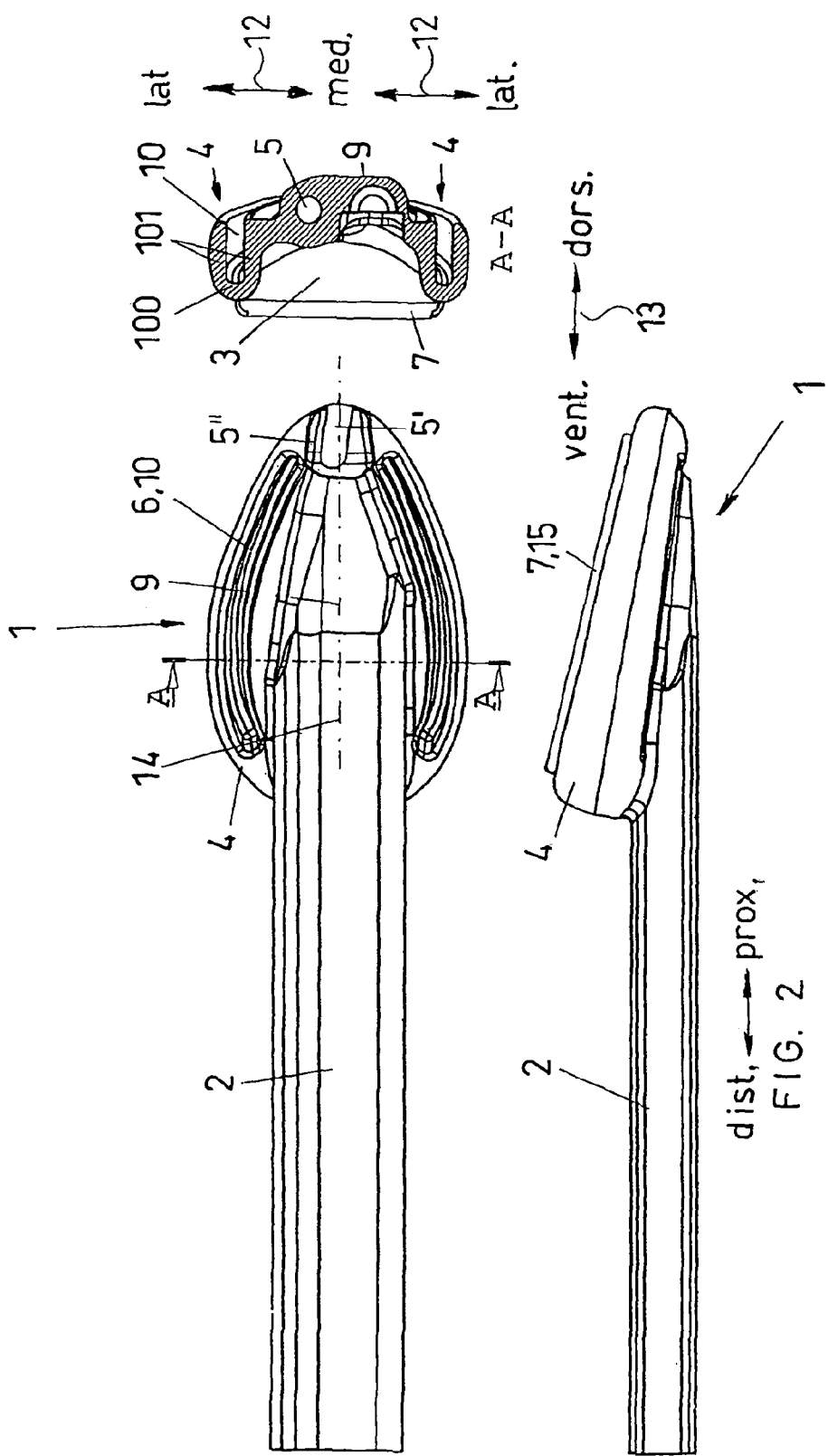

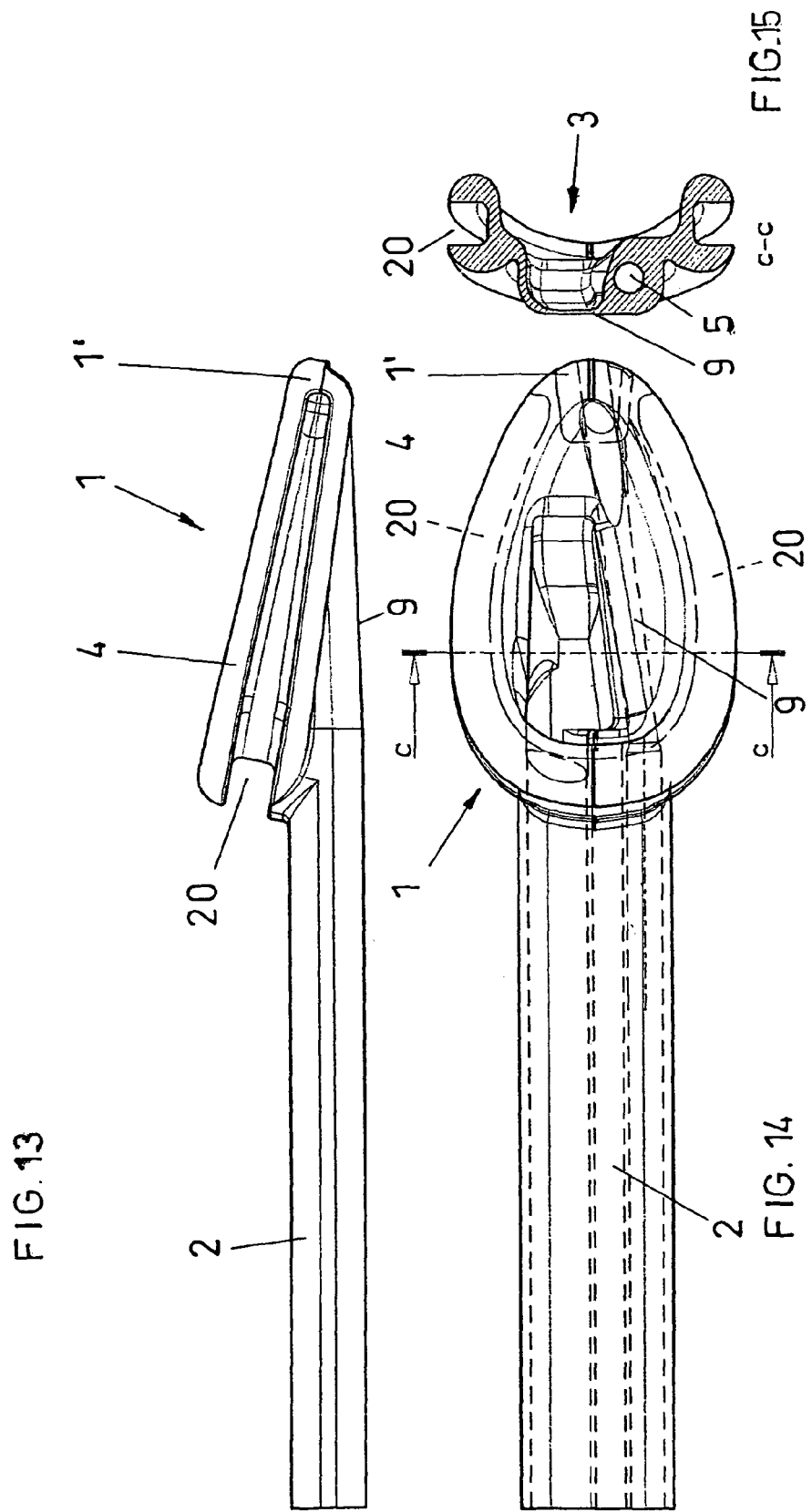

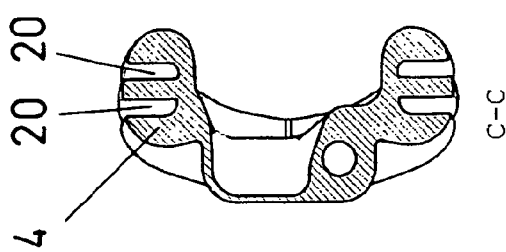
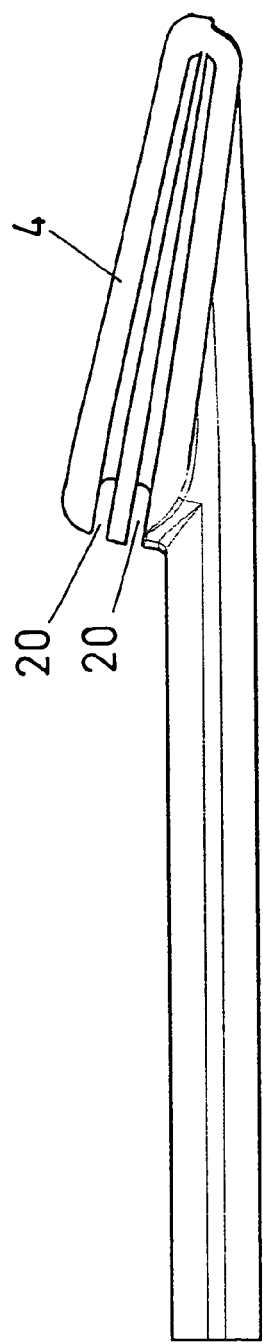
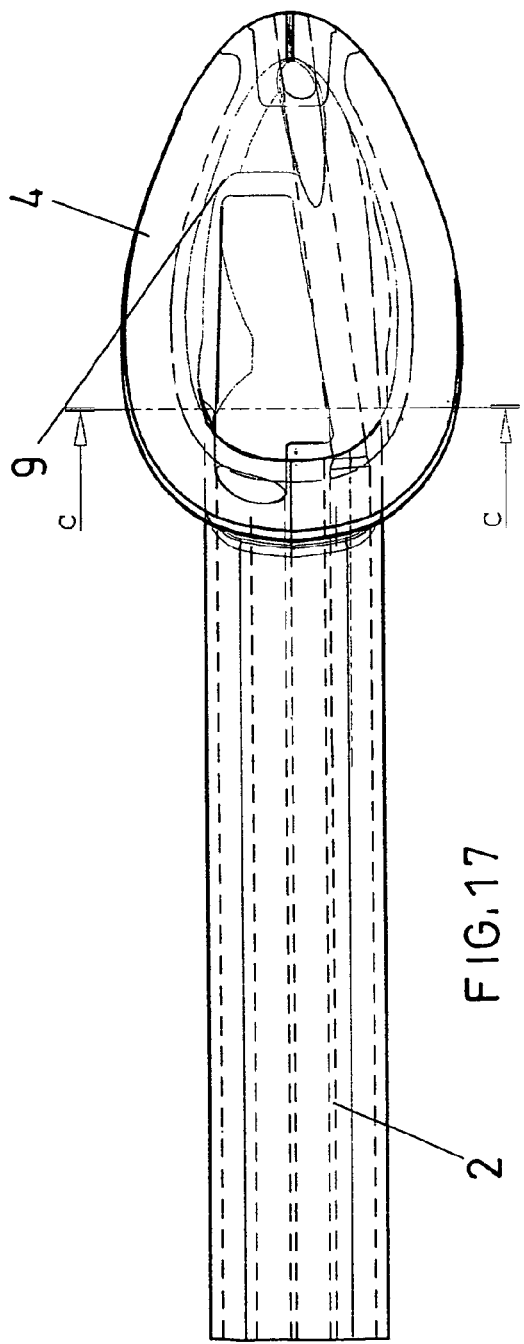

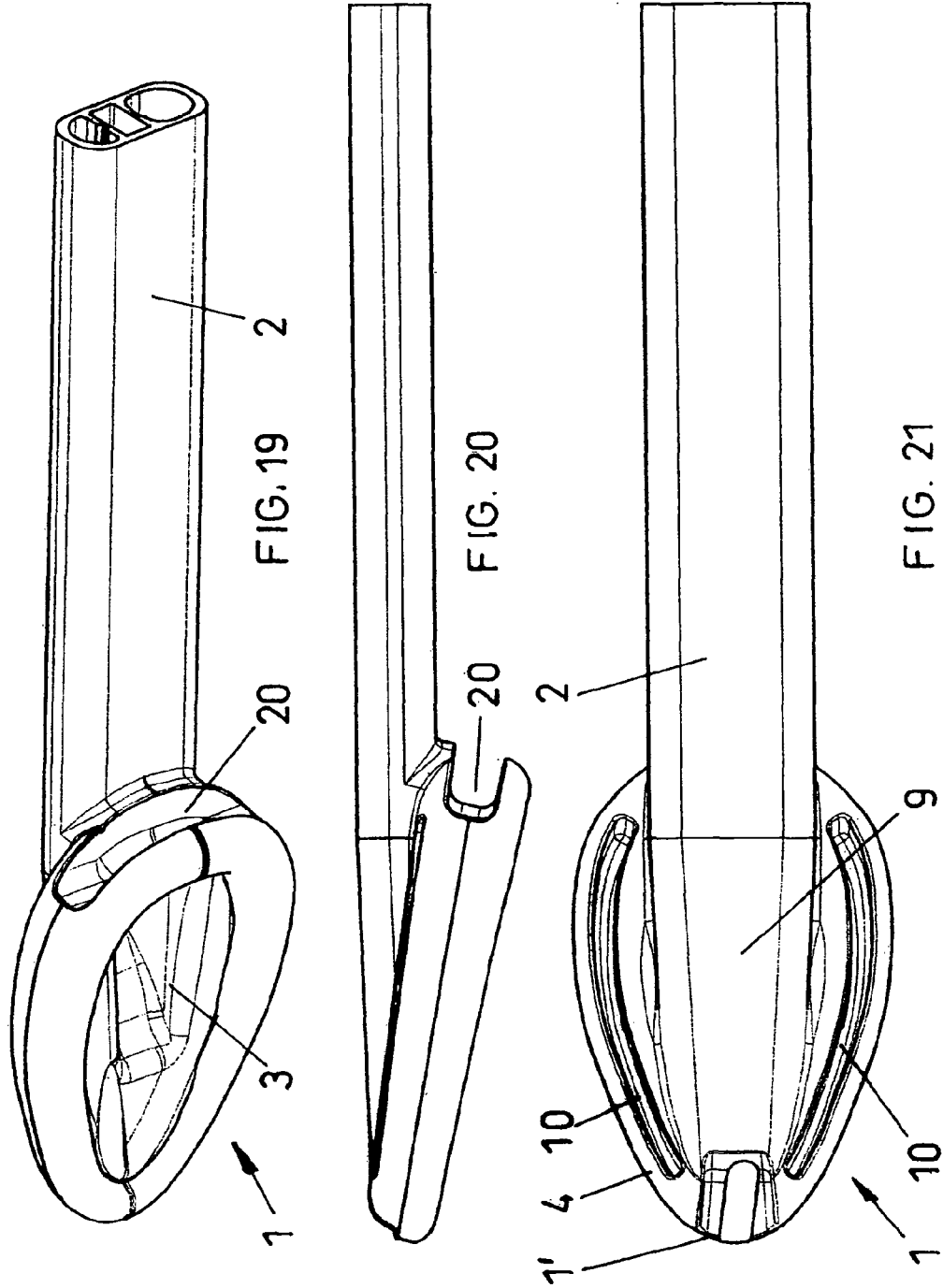

LARYNGEAL MASK HEAD

REFERENCE TO RELATED APPLICATIONS

This application is the US national phase entry of International Patent Application no. PCT/EP2013/061059, filed May 29, 2013, which claims priority to Swiss patent applications no. 00768/12, filed Jun. 4, 2012 and 01169/12, filed Jul. 26, 2012.

TECHNICAL FIELD

The present invention relates to a laryngeal mask head having a cover plate positioned dorsally and a supraglottic tube connected thereto, the laryngeal mask head having a cuff surrounding a ventral respiration chamber.

BACKGROUND

A variety of laryngeal masks based on different design principles are known and available on the market. The majority of all the laryngeal mask heads have a cover plate that is positioned dorsally and is connected to a supraglottic tube. A respiration chamber, which is surrounded by a cuff, is present on the ventral side of the laryngeal mask head. In the majority of all known laryngeal mask heads, this cuff is inflatable. Typical examples of such laryngeal masks in which the laryngeal mask head has a cover plate positioned dorsally and a ventral respiration chamber, wherein the respiration chamber is surrounded by an inflatable cuff, are disclosed, for example, in U.S. Pat. No. 5,878,745, US Patent 2003/0037790 and U.S. Pat. No. 7,040,322. Laryngeal masks in which the laryngeal mask head has a non-inflatable cuff are much less common. Such laryngeal masks are usually designed in one piece by forming the laryngeal mask head and the supraglottic tube in one piece having approximately the shape of a handheld showerhead. EP 0 389272 discloses a laryngeal mask, which may also be designed with a non-inflatable cuff, in which case this cuff has a peripheral collar facing the ventral direction to improve the seal. This laryngeal mask or laryngeal mask head is considered to be the most proximate prior art. GB Patent 2,404,863 also discloses a laryngeal mask, wherein the laryngeal mask and the supraglottic tube are connected to one another in one piece here. The adjustment in the shape of this laryngeal mask is also accomplished here, as in the aforementioned EP 389272, by means of a peripheral collar having an integrally molded cuff.

On the other hand, EP 1875937 discloses a type of laryngeal mask similar to that in the aforementioned GB Patent 2,404,863, wherein the seal here is implemented essentially by an improved anatomically adjusted shape. Ultimately reference is also made to EP 1938855, in which a supporting ring is integrally molded on the cuff by means of a thin-walled elastic connection instead of the peripheral collar.

All the laryngeal masks having non-inflatable cuffs described here provide only a certain elastic adjustment, which is performed in the ventral-dorsal direction. None of the aforementioned approaches discloses an adjustability in size and shape using only non-pneumatic means in the lateral-medial and/or ventral-dorsal directions.

SUMMARY

The object of the present invention is therefore to create a laryngeal mask head, which can be manufactured in a compact one-piece design by injection molding and allows an adjustment of shape in the lateral-medial direction. This object is achieved by a laryngeal mask head made of plastic having a cover plate positioned dorsally and a supraglottic tube connected thereto, wherein the laryngeal mask head has a cuff surrounding a ventral respiration chamber, characterized in that the cuff has only non-pneumatic means for flexible size adjustment in the medial-lateral and/or dorsal-ventral direction.

This size adjustment is preferably accomplished by the fact that the non-pneumatic means are open channels, wherein the channels for medial-lateral size adjustment have a ventral-dorsal direction of penetration or depth extension, and the channels that are provided for ventral-dorsal size adjustment have a medial-lateral direction of penetration or depth extension.

The resilient effect of the channels is obtained through the choice of materials, on the one hand, and, on the other hand, by determination of the wall thickness of the side walls of the channel. However, one is limited to certain given factors with respect to the choice of materials and also with respect to the wall thickness embodiment, and resiliently supporting members, by means of which the spring force of the channels can be influenced, are proposed accordingly. These members are explained in the additional claims.

Such a laryngeal mask head may of course also be designed in one piece with the supraglottic tube connected to it.

BRIEF DESCRIPTION OF THE DRAWINGS

A preferred exemplary embodiment of the subject matter of the invention is illustrated in the drawings and described on the basis of the accompanying description with reference to the accompanying drawings, in which:

FIG. 1 shows a laryngeal mask in the overall view of the cover plate from above, and FIG. 2 shows the same laryngeal mask in a side view, while FIG. 3 shows a vertical section through the laryngeal mask head along line A-A as shown in FIG. 1.

FIGS. 4-7 show systematic sectional drawings through the channel with different means for medial-lateral size adjustment, while

FIG. 12 shows an enlarged vertical section through a variant of the laryngeal mask head according to the invention, having means for medial-lateral size adjustment, while FIG. 13 shows another variant of the laryngeal mask head having means for ventral-dorsal size adjustment in a side view, FIG. 14 shows a view from above, and FIG. 15 shows a vertical section along line C-C in FIG. 14.

FIG. 16 shows another variant, which has the same design as the embodiment according to FIGS. 13-15, but in this case it has two parallel grooves in the side view, and FIG. 17 again shows a view from above, and FIG. 18 again shows a vertical section along line C-C in FIG. 17.

FIG. 19 shows the laryngeal mask head having a tube integrally molded onto it in one piece in a perspective diagram of the last variant of the invention.

FIG. 20 shows a side view, and

FIG. 21 shows a view in the direction of the cover plate.

DETAILED DESCRIPTION

Figure 4:
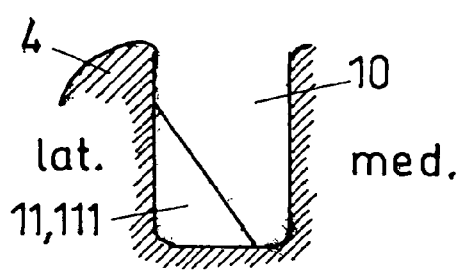

FIGS. 1-3 show a laryngeal mask designed according to the invention. It consists of the two main components, namely the laryngeal mask head 1 and the supraglottic tube 2 connected to it. These two parts may either be manufactured individually or may be manufactured together in one piece. In the view toward the dorsal side of the laryngeal mask head 1 shown in FIG. 1, the cover plate 9, which is a one-piece component of the laryngeal mask head here, followed by the supraglottic tube 2 at the center. A respiration chamber 3 is situated beneath the cover plate 9 and thus in the ventral direction. This respiration chamber 3 is bordered on all sides by a peripheral cuff 4. An esophageal passage 5 runs in the cover plate 9. This is of course only one optional possibility and is not essential for implementation of the present invention. This esophageal passage 5 enters the laryngeal mask head 1 at 5'. There is an open channel, which leads away over the cuff 4 accordingly. Supports 5' are present at the side of this channel, reinforcing the cuff in this region and thus preventing kinking of the laryngeal mask head 1 during insertion. Means 6, which serve to permit a medial-lateral size adjustment, are embedded in the cuff 4 running on both sides of the cover plate 9. Such means for size adjustment in the medial-lateral direction may include peripheral and protruding ribs (not shown here), but, as also shown here, these means 6 for medial-lateral and/or dorsal-ventral size adjustment may also preferably be provided accordingly in the cuff 4 and channels 10 running in their longitudinal direction. In the exemplary embodiment shown here, these channels 10 run from the region of insertion of the tube 2 into the laryngeal mask head 1 until emerging in the region in the esophageal passage 5 and continuing beyond the cuff. The direction of penetration of the channels 10 in this example runs in the ventral-dorsal direction. If the laryngeal mask head 1 is designed without an esophageal passage, then the channel 10 may in principle also extend around the cover plate 9. However, this is preferably avoided, so as not to thereby weaken the tip of the laryngeal mask head 1. Furthermore, no size adjustment in the distal-proximal direction is necessary.

The sections of channel running on both sides of the cover plate 9 have approximately a partially elliptical path guide. When discussing the channel 10 below with respect to this embodiment according to FIGS. 1-3, FIG. 12 and FIGS. 19-21, this is also understood to include the two channel sections on the two sides of the cover plate 9. Both sides of the central axis 14 are also mentioned here because the laryngeal mask head 1 has an approximately symmetrical shape here in the view from above.

These channels 10, as mentioned previously, here represent the means 6 for medial-lateral size adjustment. This direction is represented symbolically with the double arrow 12. A double arrow 13 running perpendicular to this arrow in the longitudinal direction indicates the ventral-dorsal direction, and the means 7 lead in this direction to adjustment in the ventral-dorsal direction. In the example shown here, these means 7 consist of a peripheral resilient sealing lip 15. Such resilient sealing lips for sealing elastic adjustment in the ventral-dorsal direction are also already known from the documents cited in the introduction.

The resilient effect of the means 6 can be determined through the choice of the material, i.e., the choice of the plastic used here, but also through the geometric design, namely the wall thickness of the channel 10. This channel 10 has a bottom 100 and side walls 101. The thickness of the bottom as well as that of the side walls can of course be defined in almost any way and the softness or hardness of the resilient effect of the means 6 is designed for medial-lateral size adjustment accordingly. Nevertheless, one is not as totally free in the choice of materials specifically in the medical technical field as one might like and also one is of course bound to anatomical relationships with respect to the geometry. To be able to nevertheless adjust the resilient effect in the lateral-medial or dorsal-ventral direction, various elastic supporting members 11 are proposed and explained with reference to FIGS. 4-11.

In the description of the following simplified representation of the channel, the terms "lateral" and "medial" are used according to the position shown here. Similarly, one could speak of dorsal and ventral side walls in the case of a channel represented as horizontal.

A first variant is illustrated in FIG. 4. The channel 10 is represented purely symbolically in cross section. This U-shaped channel 10 has an elastic supporting member 11, as mentioned above. This member 11 in the embodiment according to FIG. 4 consists of a supporting rib 111, which extends upward at an inclination from the bottom 100 of the channel 10 to one of the side walls 101. Depending on which spring characteristic one would like to thereby create, the supporting rib 111 is supported on the side wall 101 that is closer to the center, i.e., situated in the radial direction, or on the opposite side wall, which represents the lateral side wall. If only the lateral side wall is supported, then it becomes stiffer accordingly and thus forms a greater spring pressure in the lateral direction, or the supporting ribs 111 are supported on the medial side, so that the side wall is reinforced while the lateral side wall may be slightly deformable accordingly.

Figure 5:
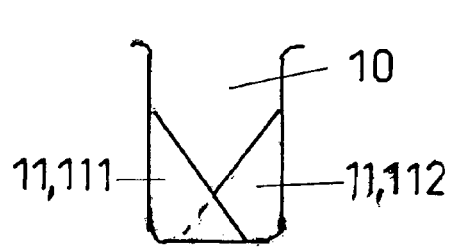

However, it is also quite possible to provide such supporting ribs 111, 112 on both side walls, as illustrated symbolically in FIG. 5. The channel 10 in particular will achieve an increased stiffness in the region of its bottom 100 in this way, while the upper region, i.e., the dorsal region, of the channel is practically unreinforced.

Figure 6:
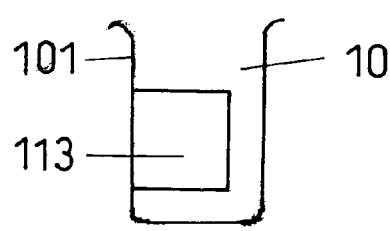

The variant according to FIG. 6 illustrates one possibility, in which a supporting lobe 113 is integrally molded as an elastic supporting member 111 that extends from one side wall in the direction of the other side wall but does not completely cross the channel. In order for such a traversing supporting rib 113 to be appropriate, it should traverse at least 50% of the width of the channel. Such a supporting lobe 113 is integrally molded only on the side wall but not on the bottom. The bottom therefore remains flexible. However, one disadvantage to this approach is the relatively complex production because this presupposes an injection mold with appropriate slide valves or a collapsible core.

Figure 7:
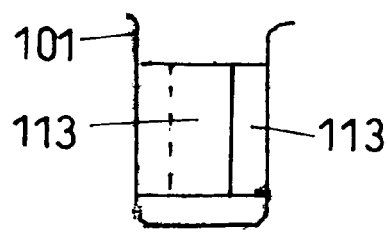

FIG. 7 shows one approach of the same type but it uses supporting lobes 113, which are integrally molded alternately on one side wall 101 and then on the other side wall.

Figure 8:
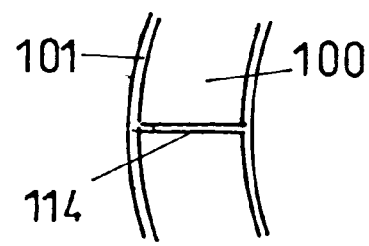
FIGS. 8-11 show partial views of channels having supporting walls of various designs.
Figure 9:
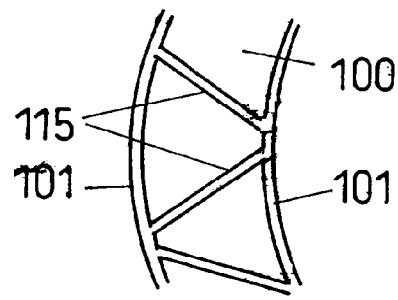

The channel 10 in FIGS. 4-7 is always represented symbolically in cross section, but in the variants of embodiments according to FIGS. 8-11, this channel is shown in a view from above, naturally including only a partial region of the channel. This is therefore a view of the bottom 100 flatly, and the side walls 101 are in turn shown only symbolically with a double line. FIG. 8 shows an approach with a supporting wall 114 illustrated as an elastic supporting member 11. This supporting wall 114 is now integrally molded on the bottom 100 as well as on the two side walls. In the variant according to FIG. 8, the supporting wall 114 runs perpendicular to the longitudinal direction of the channel 10 in the corresponding region. Alternatively, FIG. 9 shows one approach, in which the supporting walls 15 are now shown disposed at an inclination to this longitudinal direction. However, these supporting walls 115 are of course integrally molded on both the side walls 101 and the bottom 100.

Figure 10:
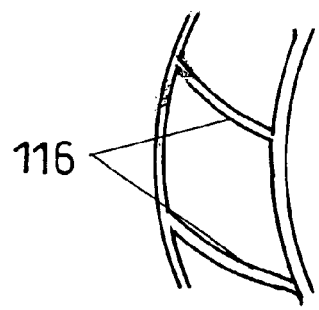
Figure 11:
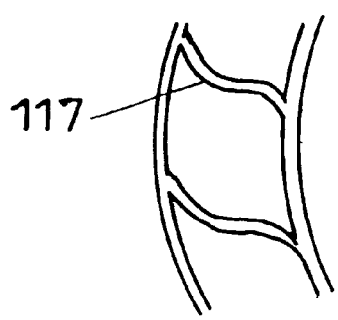

Such supporting walls naturally need not always run in a straight line. For example, FIG. 10 shows a variant illustrating the curve of the supporting walls 116. Alternatively, these supporting walls may also have an S-shape, as shown in FIG. 11, while the supporting walls that run in a straight line practically result in a greater stiffness of the side walls 101 of the channel 10 because these supporting walls undergo a change in shape only after a certain amount of deformation has occurred and then they can be deformed further. This problem does not occur with the supporting walls 116 and 117, which have a curvature.

Since the laryngeal mask head 1 is made of plastic on the whole, this also results in relative displacements between the side walls 101 of the channel 10 on insertion of the laryngeal mask. This can lead to certain blockages in unfavorable cases, which allow a spring movement only under difficult conditions, these problems are not encountered in the choice of the S-shaped curved supporting walls, such as the supporting walls 117.

Although not shown here, instead of only one channel 10, it is of course also possible to have two or more such channels running in parallel, one on each side of the cover plate in the cuff 4. In such an approach, the channels would then be designed of different lengths. The channels would then be made shorter when closer to the central axis 14 in the medial direction, while the parallel channels 10 disposed farther toward the outside in the lateral direction would be designed longer. This would result in a greater stiffness in the region close to the respiration chamber, while the flexibility would be increased further toward the outside in the lateral direction.

Figure 12:
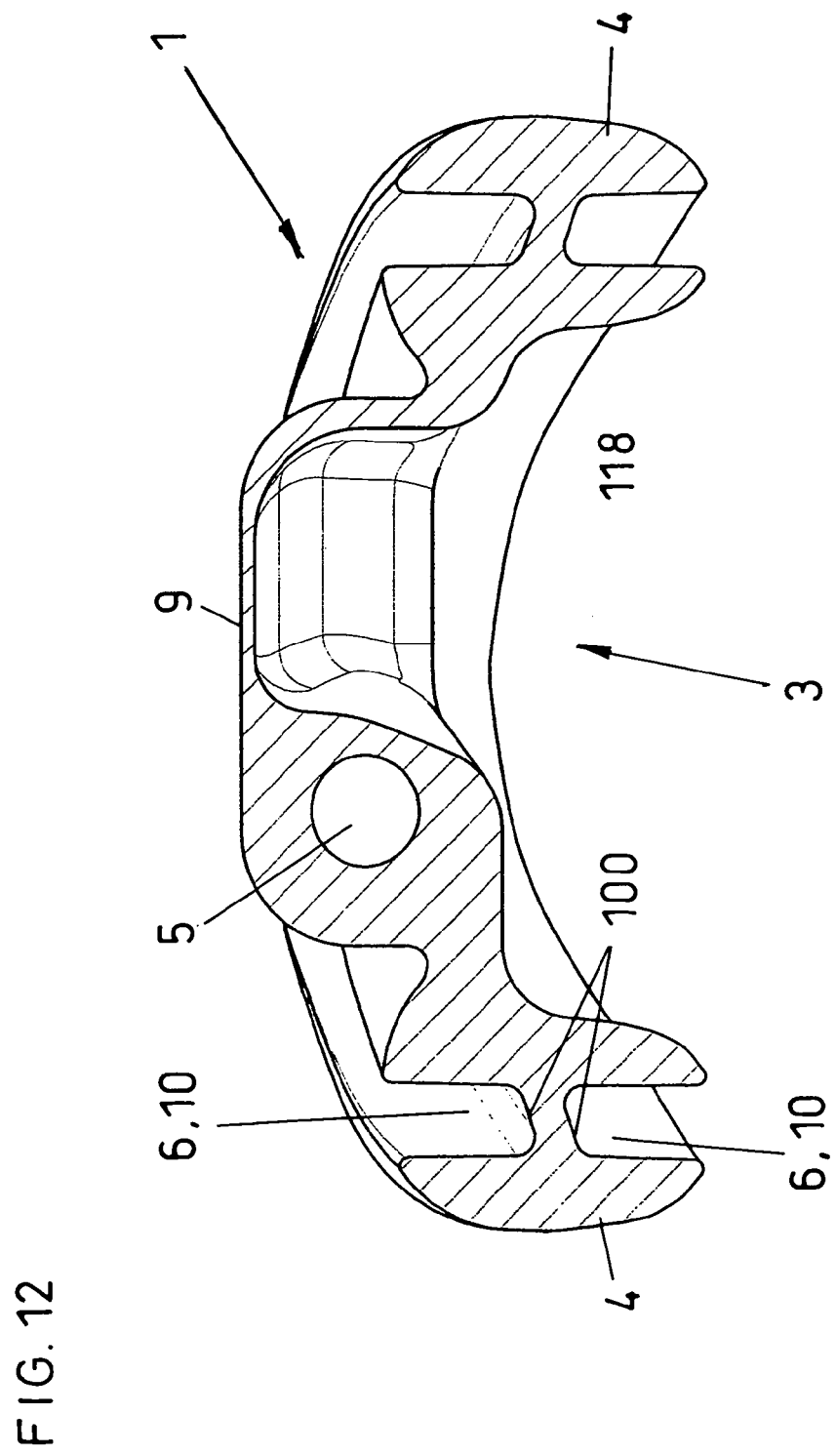

The embodiment according to FIG. 12 corresponds essentially to the embodiment according to FIGS. 1-3. In this enlarged vertical section through the laryngeal mask head 1, one can see at the top the cover plate 9 and the esophageal passage 5 running beneath it. The cuff 4 runs around the cover plate 9. In contrast with the embodiment described previously, there is not only a single channel 10 as the means for medial-lateral size adjustment, but there are two channels, which are disposed so they are aligned one above the other and have a common bottom 100. However, there is not just one channel 10 here penetrating from the dorsal direction, but there is also a channel 10 penetrating from the ventral side here. Since these two channels 10 are positioned so they are aligned one above the other, they therefore have a common connecting wall region as the bottom 100. The connecting wall 118 preferably does not run exactly medially-laterally but instead is at a slight inclination in order to facilitate the deformation with a pressure acting medially-laterally.

The cuff 4 is therefore divided into two parts on the ventral contacting side, forming a seal. This two-part design is especially advantageous because it results in practically two sealing surfaces and a higher specific pressure can be achieved at the sealing edges thanks to the smaller contact surfaces, so that an increased sealing effect is implemented.

Although all the previous embodiments have illustrated approaches having means 6 for medial-lateral size adjustment, the following figures illustrate approaches having means 7 for ventral-dorsal size adjustment. These means 7 are in turn implemented here as channels, but these channels having a lateral-medial direction of penetration into the cuff are labeled as 20. These channels 20 having the lateral-medial direction of penetration produce a ventral-dorsal size adjustment. This again shows the laryngeal mask head 1 with the supraglottic tube 2 integrally molded thereon. This tube has the ventral respiration chamber 3 and the esophageal passage 5 beneath the cover plate 9, as shown in FIG. 15. The channel 20 runs in a horseshoe shape in the cuff 4. The channel 20 is not drawn through only in the region of the tip 1'. This is possible per se but is preferably omitted, to thereby preserve a greater strength of the tip 1', which thus ensures that this tip 1' will not encourage a kinking effect.

In the embodiment according to FIGS. 16-17, two channels 20 run parallel to one another. Otherwise this approach is identical to the variant according to FIGS. 13-15. Therefore, the elements that remain the same will not be described again here. As already mentioned above, the plurality of sealing edges result in a higher specific pressure and thus an increased tightness.

Finally, a combined approach is shown in the embodiment according to FIGS. 19 to 21. The perspective view according to FIG. 19 shows only a partial channel having a depth of penetration running in the lateral-medial direction. This channel 20 is provided only in the region of insertion of the supraglottic tube 2 into the laryngeal mask head 1. In view of the increased concentration of material here, this region would otherwise be relatively stiff. In size, path and configuration, the channels 10 correspond to the variant already described with reference to FIGS. 1-3. Again in these combined embodiments, it is quite conceivable that, here again, a plurality of channels 10 running parallel to one another and/or channel sections 20 running parallel to one another may also be present here.

Thanks to the multiplicity of possible variants, which may of course also be provided with the corresponding supporting ribs, supporting lobes or straight or curved supporting walls, this yields a variety of possible combinations, which make it possible in practical terms to achieve any desired spring characteristics of the cuff. Manufacturers are given an opportunity to offer a variety of embodiments on the market with relatively minor changes in shape through the choice of the corresponding combination and/or design of the laryngeal mask head with one or more channels 10, with a ventral-dorsal direction of penetration or one or more channels 20 running parallel to one another with a lateral-medial direction of penetration.

REFERENCE LIST 1 laryngeal mask head
1' tip of the laryngeal mask head
2 supraglottic tube
3 ventral respiration chamber
4 surrounding cuff
5 esophageal passage
5" lateral support
5' esophageal inlet
6 means for medial-lateral size adjustment
7 means for ventral-dorsal size adjustment
8 peripheral sealing lip
9 cover plate
10 channel with ventral-dorsal direction of penetration
11 elastic supporting members
12 lateral-medial direction
13 ventral-dorsal direction
14 central axis
15 ventral-dorsal elastic peripheral sealing lip
20 channel with lateral-medial direction of penetration
100 bottom of the channel 101 side wall of the channel
111 supporting rib on one side
112 supporting rib on both sides
113 supporting lobe
114 supporting wall, straight
115 supporting wall, inclined
116 supporting wall, curved
117 supporting wall, S-shaped
118 connecting wall

The invention claimed is:

1. A laryngeal mask head made of plastic having a cover plate positioned dorsally and a supraglottic tube connected thereto, wherein the laryngeal mask head has a cuff surrounding a ventral respiration chamber, and wherein the cuff has non-pneumatic structures for flexible size adjustment in a medial-lateral direction and a dorsal-ventral direction, and wherein the cuff comprises at least one channel running in a medial-lateral direction.

2. The laryngeal mask head according to claim 1, wherein cuff comprises at least one ventral-dorsal channel for a medial-lateral size adjustment and at least one medial-lateral channel for a ventral-dorsal size adjustment.

3. The laryngeal mask head according to claim 2, wherein the channels for size adjustment are disposed in the cuff on both sides of a central axis of the laryngeal mask head extending in a longitudinal direction of the cuff.

4. The laryngeal mask head according to claim 2, wherein each channel comprises side walls and at least one supporting member that traverses the channel at least partially, and the at least one supporting member supports the channel side walls elastically and is integrally molded thereon.

5. The laryngeal mask head according to claim 4, wherein the at least one supporting member is a supporting rib which extends upward from a bottom of the channel to a side wall with an inclination toward a channel opening.

6. The laryngeal mask head according to claim 5, wherein one supporting rib is inclined toward a lateral or ventral side wall of the channel and one supporting rib is inclined toward the medial or dorsal side wall extending upward in alternation toward the opening.

7. The laryngeal mask head according to claim 4, wherein the at least one supporting member comprises a supporting lobe crossing the channel at least 50% to 99%, from one side wall toward an opposite side wall.

8. The laryngeal mask head according to claim 7, comprising multiple supporting lobes integrally molded on one side wall and on the opposite side wall in alternation.

9. The laryngeal mask head according to claim 4, wherein the at least one supporting member comprises supporting walls which are integrally molded on both side walls and on a bottom of the channel.

10. The laryngeal mask head according to claim 9, wherein the supporting walls are straight or curved and the channel runs vertically or at an inclination to a longitudinal direction of the supporting walls.

11. The laryngeal mask head according to claim 9, wherein the supporting walls cross the direction of longitudinal extent of the channel at different angles of inclination.

12. The laryngeal mask head according to claim 4, wherein the thickness of the side walls and the supporting members is selected to achieve a desired spring strength.

13. The laryngeal mask head according to claim 3, wherein two or more channels running parallel to one another are molded on each side of the central axis of the laryngeal mask head.

14. The laryngeal mask head according to claim 2, wherein at least two channels aligned with one another penetrate the cuff in a ventral-dorsal direction.

15. The laryngeal mask head according to claim 2, wherein the channels extend in an essentially medial-lateral direction of penetration in the form of a horseshoe in a shape of the cuff, and wherein a tip of the cuff is free of channels.

16. The laryngeal mask head according to claim 15, wherein in a region in which the tube crosses the cuff, there is at least one channel present for ventral-dorsal size adjustment, and wherein at least one channel runs on each side of the cover plate for ventral-dorsal size adjustment of the cuff.

17. The laryngeal mask head according to claim 4, wherein the at least one supporting member comprises supporting walls that are S-shaped.

* * * * *